(12) United States Patent
Beer

(10) Patent No.: US 6,169,120 B1
(45) Date of Patent: Jan. 2, 2001

(54) EXTENDED CATALYST LIFE TWO STAGE HYDROCARBON SYNTHESIS PROCESS

(75) Inventor: Gary L. Beer, Plano, TX (US)

(73) Assignee: Syntroleum Corporation, Tulsa, OK (US)

( * ) Notice: Under 35 U.S.C. 154(b), the term of this patent shall be extended for 0 days.

(21) Appl. No.: 09/397,474

(22) Filed: Sep. 17, 1999

(51) Int. Cl.⁷ .................................................. C07C 27/00
(52) U.S. Cl. .......................... 518/715; 518/700; 518/706
(58) Field of Search .................................. 518/700, 706, 518/715

(56) References Cited

U.S. PATENT DOCUMENTS

| | | | |
|---|---|---|---|
| 4,042,614 | 8/1977 | Vannice et al. | 260/449 R |
| 4,088,671 | 5/1978 | Kobylinski | 260/449.6 R |
| 4,159,995 | 7/1979 | Haag et al. | 260/450 |
| 4,171,320 | 10/1979 | Vannice et al. | 260/449 R |
| 4,279,830 | 7/1981 | Haag et al. | 518/700 |
| 4,443,561 | 4/1984 | Boelema et al. | 518/704 |
| 4,477,595 | 10/1984 | Madon | 518/715 |
| 4,547,609 | 10/1985 | Dessau | 585/517 |
| 4,568,663 | 2/1986 | Mauldin | 502/325 |
| 4,585,798 | 4/1986 | Beuther et al. | 518/715 |
| 4,599,481 | 7/1986 | Post et al. | 585/700 |
| 4,624,968 | 11/1986 | Kim et al. | 518/707 |
| 4,681,867 | 7/1987 | Dyer et al. | 502/242 |
| 4,801,573 | 1/1989 | Eri et al. | 502/302 |
| 4,973,453 | * 11/1990 | Agee | 422/190 |
| 5,028,634 | * 7/1991 | Flato | 518/707 |
| 5,498,638 | 3/1996 | Long | 518/706 |
| 5,905,094 | 5/1999 | Chang et al. | 518/700 |

OTHER PUBLICATIONS

"Fischer–Tropsch Synthesis: Differential Reaction Rate Studies with Cobalt Catalyst"; R.B. Anderson, A. Krieg, R.A. Friedel and L.S. Mason, *Industrial and Engineering Chemistry*, Oct., 1949, pp. 2189–2197.

\* cited by examiner

*Primary Examiner*—Johann Richter
*Assistant Examiner*—J. Parsa
(74) *Attorney, Agent, or Firm*—Baker Botts, L.L.P.

(57) ABSTRACT

An extended catalyst life two-stage hydrocarbon synthesis process wherein a first synthesis gas stream is reacted in a first stage reactor in the presence of a suitable catalyst to produce liquid hydrocarbon products and a gaseous stream; the gaseous stream is cooled and water and liquid hydrocarbons are separated from the gaseous stream to produce a second synthesis gas stream which is then passed to a second stage reactor for the production of additional liquid hydrocarbons.

16 Claims, 1 Drawing Sheet

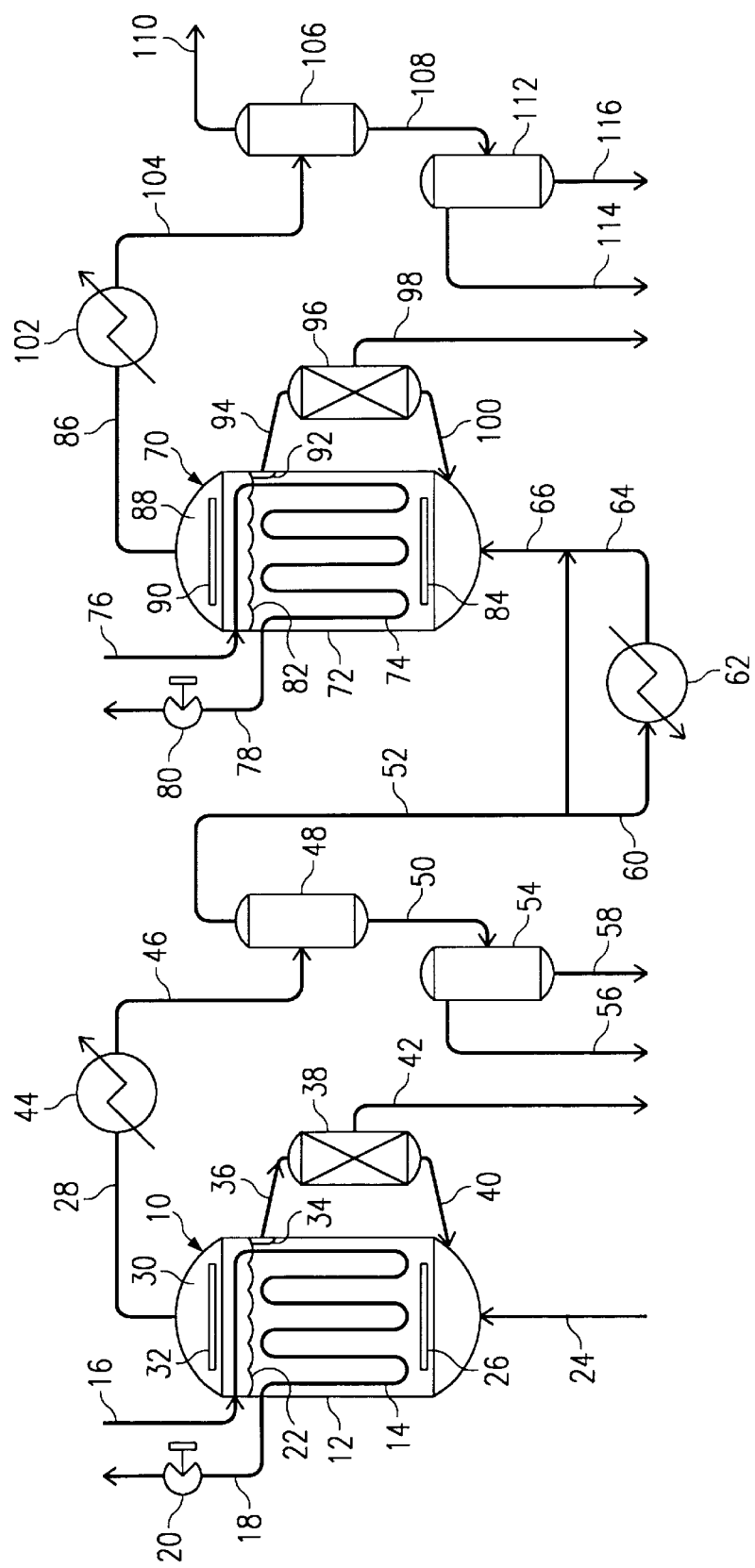

EXTENDED CATALYST LIFE TWO STAGE HYDROCARBON SYNTHESIS PROCESS

FIELD OF THE INVENTION

This invention relates to a two-stage Fischer-Tropsch synthesis process which provides for extended catalyst life. The carbon monoxide conversion in each of a first and second stage is controlled to a conversion of about 40 to about 60 percent of the carbon monoxide in each stage. Additional stages can be used if desired.

BACKGROUND OF THE INVENTION

Fischer-Tropsch hydrocarbon synthesis catalysts have been studied widely by a number of researchers in recent years. Preferred processes are currently slurry bubble column processes wherein the catalysts used typically comprise cobalt or ruthenium, cobalt and ruthenium or promoted cobalt catalyst. The catalysts are supported on a variety of supports but generally are supported on supports selected from metal oxides such as alumina, silica, titanium, silica-alumina and the like.

Promoters can be used to enhance the activity of or the stability of cobalt or ruthenium catalysts. For example ruthenium has been used to promote cobalt catalysts supported on either titania or alumina, see U.S. Pat. Nos. 4,568,663 and 4,801.573 respectively. Supported ruthenium catalysts are also quite useful for hydrocarbon synthesis (see U.S. Pat. Nos. 4,477,595; 4,171,320, and 4,042614). Also, ruthenium and zirconium have been used to promote cobalt supported on silica (see U.S. Pat. Nos. 4,088,671, 4,599,481, and 4,681,867). Two-stage hydrocarbon synthesis was disclosed in U.S. Pat. No. 4,443,561 relating to hydrogen:carbon monoxide ratios, but making no differentiation based on the pressure in each reaction stage. This process also requires that a hydrogen-rich gas be added between the stages.

Other two stage hydrocarbon synthesis processes have been reported in the literature. U.S. Pat. Nos. 4,547,609, 4,279,830, and 4.159,995 use an iron-based first stage catalyst for hydrocarbon synthesis and a second stage catalyst having activity for aromatization. Also U.S. Pat. No. 4,624,968 employs an iron-based first stage catalyst for producing olefins and a second stage catalyst for converting olefins to paraffins with additional CO and hydrogen. All of these systems are based on dual function catalyst systems, that is, where the first stage catalyst is active for a specific chemical reaction and the second stage catalyst is active for a different chemical reaction. However, none of these systems involve a two-stage process in which catalysts of essentially equivalent functionality are tailored to the specific operating conditions of each stage.

Hydrocarbon synthesis processes are known to be plagued with several problems. Of these problems, obtaining high conversion and dissipating heat are among the foremost. Since hydrocarbon synthesis is an exothermic reaction, heat must be removed from the reactor to avoid hot spots, catalyst deactivation, and loss of selectivity at higher temperatures. There is usually a preferred temperature range for operating the process which leads to the optimum selectivity to desired higher hydrocarbon products. Lack of efficient heat removal can lead to much higher temperatures in the reactor which, while increasing carbon monoxide conversion, severely debits the selectivity to preferred higher hydrocarbons. At the same time, increasing conversion generates more heat and thus, a greater burden on heat exchange facilities. Thus, the goals of high conversion and efficient heat transfer tend to oppose each other. To alleviate the problem, lower conversion in a first stage can be accommodated, thereby reducing the heat load in the first stage. However, this reduced conversion must be made up in the second stage.

It has been observed that when high conversions are achieved, the presence of the resulting large amounts of water are detrimental to catalyst life. It would be desirable to achieve the higher conversion levels without the corresponding decrease in catalyst life as a result of the increased water levels.

SUMMARY OF THE INVENTION

According to the present invention, an extended catalyst life two-stage hydrocarbon synthesis process is provided and comprises reacting a first synthesis gas stream comprising hydrogen, carbon monoxide and from about 30 to about 60 volume percent nitrogen in a first stage reactor in the presence of a catalyst comprising cobalt, ruthenium or cobalt and ruthenium supported on a support comprising at least one inorganic metal oxide selected from Group IIIA, IIIB. IVB, VB, VIB and VIIB metal oxides, alumina, silica, silica-alumina and combinations thereof at a temperature from about 380 to about 500° F. at pressure from about 15 to about 25 atmospheres at a carbon monoxide conversion from about 40 to about 60 percent to produce liquid hydrocarbon product; recovering at least a portion of the liquid hydrocarbon product stream from the first stage reactor; recovering a gaseous stream comprising gaseous hydrocarbons, hydrogen, carbon monoxide and nitrogen from the first stage reactor; cooling the gaseous stream to a temperature below about 150° F. to produce a cooled gaseous stream; separating water and hydrocarbons condensed from the cooled gaseous stream to produce a second synthesis gas stream comprising hydrogen, carbon monoxide and nitrogen; and reacting the second synthesis gas stream in a second stage reactor in the presence of a catalyst comprising cobalt, ruthenium or cobalt and ruthenium supported on an inorganic metal oxide selected from Group IIIA, IIIB, IVB, VB, VIB and VIIIB metal oxides, alumina, silica, silica-alumina and combinations thereof from about 380 to about 500° F. and at a pressure from about 15 to about 25 atmospheres at a carbon monoxide conversion from about 40 to about 60 percent to produce liquid hydrocarbon products.

Particularly preferred catalysts are catalysts comprising cobalt supported on alumina.

The gaseous stream leaving this second stage reactor may be treated for the removal of water and liquid hydrocarbons and passed as a synthesis gas stream to a third stage reaction zone.

BRIEF DESCRIPTION OF THE DRAWINGS

The Figure is a schematic diagram of an embodiment of the process of the present invention.

DESCRIPTION OF THE PREFERRED EMBODIMENTS

The Figure is a schematic diagram of an embodiment of the present invention including a first stage reactor 10 and a second stage reactor 70. First stage reactor 10 comprises a vessel 12 which includes a plurality of heat exchange tubes 14 for the removal of heat. Water is supplied through a line 16 to heat exchange tubes 14 and stream is recovered through a steam line 18. A back pressure control valve 20 positioned in a line 18 enables the control of the steam pressure thereby regulating the temperature in vessel 12. Vessel 12 is a slurry bubble column reactor which contains a liquid comprising primarily Fischer-Tropsch reaction liquid products in which catalyst particles having a particle size diameter of less than 100 microns are suspended. The catalyst particles are fluidized in the liquid by a synthesis gas stream passed into vessel 12 via a line 24. The synthesis gas is dispersed as a series of small bubbles for movement upwardly through vessel 12 through a sparger 26. The slurry level is maintained at a level 22 to provide a headspace 30 which contains a screen or baffle 32 positioned to prevent the passage of liquids overhead. An overhead gaseous stream is recovered through a line 28.

A liquid product is recovered from vessel 12 by positioning a weir 34 in vessel 12 below liquid level 22 so that liquid can collect in weir 34 and de-gas thereby increasing its density. The more dense liquid then flows through a line 36 to a filter 38 where a liquid product comprising primarily $C_{17+}$ hydrocarbon liquids is recovered via a line 42. The slurry from which the liquids have been recovered via line 42 is returned via a line 40 to a lower portion of vessel 12.

The synthesis gas charged to vessel 12 in the embodiment shown in the Figure is typically produced by an autothermal reactor or the like. In some processes oxygen is used as the primary oxidant. In such instances, the synthesis gas stream will contain carbon monoxide, carbon dioxide and water unless the water has been removed prior to charging the synthesis gas stream to vessel 12. Alternatively, the synthesis gas may be produced by using air or oxygen-enriched air as the oxidant gas stream. In such instances the synthesis gas stream will contain major quantities, i.e., from about 40 to about 50 percent nitrogen as charged to vessel 12. Water may also be removed from synthesis gas produced by the use of air or oxygen-enriched air as the oxidant gas.

The Figure will be discussed by reference to the use of a synthesis gas stream produced by the use of air or oxygen-enriched air (referred to as "air") as the oxidant.

The gaseous stream in line 28 comprises gaseous hydrocarbons, hydrogen, carbon monoxide and nitrogen. No liquid products are recovered in this line since the liquid products are recovered in filter 38 at a rate sufficient to maintain the liquid level 22 in vessel 12 at a desired level. All liquid recovery from vessel 12 is via filter 38. The gaseous stream in line 28 is passed to a heat exchanger 44 where the temperature is reduced to below about 150° F. Preferably the temperature is reduced to a temperature of about less than about 100° F. The cooled gaseous stream is then passed via a line 46 to a separator 48 where a second synthesis gas stream is recovered via a line 52 and comprises hydrogen, carbon monoxide and nitrogen. A liquid stream is recovered through a line 50 and passed to a separator 54 where the recovered liquids are separated into a hydrocarbon stream comprising primarily $C_5$–$C_{17}$ hydrocarbons which are recovered through a line 56 and water which is recovered through a line 58. The second synthesis gas stream may be passed via line 52 via a line 60 to a heat exchanger 62 where it is heated to a suitable temperature for charging to second reactor 70 via a line 64 and a line 66. Typically the gas if heated, is heated to a temperature of about 400 to about 500° F. Alternatively once operation has been begun the synthesis gas mixture maybe passed through line 52 directly to line 66 without heating. The heat required to increase the temperature of the synthesis gas from 100° F. to reactor temperature is slight and the reactions in reactor 70 are exothermic. Accordingly heating will not be necessary in most instances after reactor 70 is in operation. Reactor 70 comprises a vessel 72 including a plurality of heat exchange tubes 74 which are supplied with water via a line 76 with steam being recovered through a line 78. A back pressure control valve 80 in line 78 controls the pressure in heat exchange tubes 74 thereby regulating the temperature in vessel 72. A sparger 84 is positioned in the lower part of vessel 72 to disperse the synthesis gas into the slurry for movement upward through vessel 72 as finely dispersed bubbles. A second gaseous stream is recovered through an overhead line 86 from a headspace 88. A screen or baffle 90 is positioned in headspace 88 to prevent the passage of liquids into line 86. A weir 92 is used to de-gas a portion of the slurry so that the de-gassed slurry can be withdrawn through a line 94 and passed through a filter 96 where a liquid product comprising primarily $C_7+$ hydrocarbons is removed through a line 98. The slurry from which the product has been removed is passed via a line 100 back to vessel 72. The gaseous stream in line 86 is passed to a heat exchanger 102 where it is cooled to a temperature from about 100 to about 150° F. and preferably to a temperature of about 100° F. and then passed via a line 104 to a separator 106. In separator 106 a third synthesis gas is separated via a line 110 with a liquid stream being recovered through a line 108. The liquid stream is passed to a separator 112 where a hydrocarbon liquid stream comprising primarily $C_5$–$C_{17}$ hydrocarbons is separated and recovered via a line 114 and a water stream is separated and recovered via a line 116.

The third synthesis gas stream in line 110 maybe passed to further reaction in a third reactor of the same type shown for reactor 10 and reactor 70. Alternatively this gas stream may be passed for use as a fuel or the like.

The present process is particularly adapted to the use of a synthesis gas containing nitrogen. Such synthesis gas streams are not well adapted to recycle to increase the conversion rate of the gases.

In the practice of the processes of the type shown, water is generally considered to be an undesirable contaminant. While some water may be accommodated in some instances, the amounts of water produced at conversion rates greater than about 60 percent in a given reactor are considered to be detrimental to the catalyst. Since water is a reaction product of the hydrogenation of carbon monoxide to produce hydrocarbons, it is inevitable that water will be present in the slurry but quantities less than that produced at conversion from about 40 to about 60 percent of the carbon monoxide do not appear to be detrimental to the catalyst. Further it is generally considered that very high conversions of carbon monoxide tend to result in a more rapid deactivation of the catalyst because of other unidentified contaminants produced at the higher conversions.

According to the present invention, lower conversions are used in each of the reactors with the net result that a relatively high overall conversion is achieved in the overall process. With conversions of 40 to 60 percent being used in each of the reactors, it is readily calculated that conversions as high as 84 percent may be achieved. The achievement of this conversion in two vessels eliminates the need for high conversion in either vessel and limits the amount of water present in each vessel. Particularly, it has been observed that when water to carbon monoxide greater than 0.60 are present it is not uncommon to find more rapid catalyst deactivation. Similarly when the water to carbon monoxide plus hydrogen ratio is greater than about 1.0 to 1.5 similar results have been noted. This effect has been particularly pronounced when cobalt on alumina catalyst have been used. According to the present invention, the water is removed well before these levels are attained. As a result extended catalyst life is maintained while continuing to maintain a high conversion of the synthesis gas. The process is particularly effective with synthesis gas produced by the use of air as an oxidant since it is not feasible to recycle the synthesis gas to any substantial extent. Conversely, synthesis gas produced by the use of oxygen as the oxidant can be recycled to achieve higher conversions but the presence of the water at these levels is still undesirable.

The catalyst used in the present invention comprises cobalt, ruthenium or cobalt and ruthenium supported on a support comprising an inorganic metal oxide selected from Group IIIA, IIIB, IVB, VB, VIB and VIIIB metal oxides, alumina, silica, silica-alumina and combinations thereof. The catalyst used in reactor 10 and in reactor 70 may be the same or different within the parameters set forth herein for the catalyst. Preferably the catalyst support comprises primarily alumina, titania, silica, silica-alumina, and combinations thereof with the preferred support comprising alumina. As noted previously the catalyst used in both reactors 10 and 70 may be of the same composition or may be of different compositions within the parameters set forth herein. Further the catalyst may include a promoter. The promoter may be selected from those known to those skilled in the art for use with supported cobalt, ruthenium or cobalt and ruthenium catalysts. Suitable promoters are selected from a group consisting of zirconium, titanium, thenium, cerium, hafnium, ruthenium and uranium. A preferred catalyst is cobalt supported on alumina.

The liquid hydrocarbon products recovered from the process may be processed together or separately. The products recovered through lines 56 and 114 comprise primarily $C_5$–$C_{17}$ hydrocarbons and the product hydrocarbons recovered through lines 42 and 98 comprise primarily $C_{17}+$ hydrocarbons. These products are suitably processed for use as a variety of fuels, as chemical feedstocks and the like as known to those skilled in the art.

While not shown in the drawing, the synthesis gas stream recovered through line 110 may be passed to further reaction in a third reactor similar to reactors 10 and 70. Whether a third reactor is used is a question of economics and if the conversion of the synthesis gas in the third reactor produces a significant amount of product for recovery then a third reactor may be used. The use of a fourth reactor is also possible if economically feasible.

The reaction of the synthesis gas in reactor 10 and in reactor 70 are at suitable rates for the efficient operation of these two reactors. The reduced synthesis gas concentration in reactor 70 has not been found to be sufficiently detrimental to the reaction rate to limit the effectiveness of reactor 70.

According the process of the present invention is particularly effective with synthesis gas produced by the use of air or oxygen-enriched air as an oxidant and with cobalt supported on alumina catalyst. Notwithstanding the increased effectiveness of the present process under these conditions it is believed that the process also provides process conditions which are effective with other catalysts to increase catalyst life and to effectively convert synthesis gas to liquid hydrocarbon products.

Having thus described the present invention by reference to certain of its preferred embodiments, it is noted that the embodiments described are illustrative rather than limiting in nature and many variations and modifications are possible within the scope of the present invention.

Having thus described the invention, I claim:

1. An extended catalyst life, two-stage hydrocarbon synthesis process comprising:

a) reacting a first synthesis gas stream comprising hydrogen, carbon monoxide and from about 30 to about 60 volume percent nitrogen in a first slurry bubble column reactor in the presence of a catalyst having a catalyst particle size less than about 100 slurry in the second reactor.

2. The process of claim 1 wherein the catalyst in the first reactor comprises cobalt supported on alumina.

3. The process of claim 1 wherein the catalyst in the first reactor comprises cobalt supported on alumina and wherein the catalyst in the first reactor further comprises a promoter.

4. The process of claim 3 wherein the promoter is selected from the group consisting of zirconium, titanium, rhenium, cerium, hafnium, ruthenium and uranium.

5. The process of claim 1 wherein the catalyst in the second reactor comprises cobalt supported on alumina.

6. The process of claim 1 wherein the catalyst in the second reactor comprises cobalt supported on alumina and wherein the catalyst in the second reactor further comprises a promoter.

7. The process of claim 6 wherein the promoter is selected from the group consisting of zirconium, titanium, rhenium, cerium, hafnium, ruthenium and uranium.

8. The process of claim 1 wherein the catalyst in the first reactor and the second reactor are of the same composition.

9. The process of claim 1 wherein the liquid hydrocarbon stream recovered from the first reactor comprises primarily $C_{17}+$hydrocarbons.

10. The process of claim 1 wherein the liquid hydrocarbon stream recovered from the second reactor comprises primarily $C_{17}+$hydrocarbons.

11. The process of claim 1 wherein the gaseous stream is cooled to a temperature below about 150° F.

12. The process of claim 1 wherein the hydrocarbons separated from the cooled gaseous stream comprise primarily $C_5$–$C_{17}$ hydrocarbons.

13. The process of claim 1 wherein a liquid hydrocarbon stream comprising primarily $C_{17}+$hydrocarbons is recovered from the second reactor.

14. The process of claim 1 wherein a second gaseous stream comprising gaseous hydrocarbons, hydrogen, carbon monoxide and nitrogen is recovered from the second reactor and cooled to a temperature less than about 150° F. to produce a second cooled gaseous stream.

15. The process of claim 14 wherein water and hydrocarbons comprising primarily $C_5$–$C_{17}$ hydrocarbons are separated from the second cooled gaseous stream to produce a third synthesis gas stream comprising carbon monoxide, hydrogen and nitrogen.

16. The process of claim 15 wherein the third synthesis gas stream is charged to a third slurry bubble column reactor.

\* \* \* \* \*

UNITED STATES PATENT AND TRADEMARK OFFICE
CERTIFICATE OF CORRECTION

PATENT NO. : 6,169,120 B1
DATED : January 2, 2001
INVENTOR(S) : Beer

It is certified that error appears in the above-identified patent and that said Letters Patent is hereby corrected as shown below:

Column 4,
Line 14, delete [$C_7$], and insert -- $C_{17}$ --.

Column 6,
Delete Claim 1 in its entirety, and insert:
-- 1. An extended catalyst life, two-stage hydrocarbon synthesis process comprising:

a) reacting a first synthesis gas stream comprising hydrogen, carbon monoxide and from about 30 to about 60 volume percent nitrogen in a first slurry bubble column reactor in the presence of a catalyst having a catalyst particle size less than about 100 microns, the catalyst particles being suspended in a slurry comprising the catalyst particles, a liquid and hydrogen and carbon monoxide and comprising cobalt, ruthenium or cobalt and ruthenium supported on alumina, at a temperature from about 380 to about 500° F at pressure from about 15 to about 25 atmospheres at a carbon monoxide conversion from about 40 to about 60 percent to produce a liquid hydrocarbon product:
b) recovering a liquid hydrocarbon product stream from the slurry in the first reactor;
c) recovering a gaseous stream comprising gaseous hydrocarbons, hydrogen, carbon monoxide and nitrogen from the first reactor;
d) cooling the gaseous stream to a temperature below about 150°F to produce a cooled gaseous stream;
e) separating water and hydrocarbons condensed from the cooled gaseous stream to produce a second synthesis gas stream comprising hydrogen, carbon monoxide and nitrogen;
f) heating the second synthesis gas stream to a temperature from about 400 to about 500° F; and,
g) reacting the second synthesis gas stream in a second slurry bubble column reactor in the presence of a catalyst having a catalyst particle size less than about 100 microns, the catalyst particles being suspended in a slurry comprising the catalyst particles, a liquid and hydrogen and carbon monoxide and comprising cobalt, ruthenium or cobalt and ruthenium supported on alumina, at a temperature from about 380 to about 500°F and at a pressure from about 15 to about 25 atmospheres at a carbon monoxide conversion from about 40 to about 60 percent to produce liquid hydrocarbon products and recovering a liquid hydrocarbon product stream from the slurry in the second reactor. --

UNITED STATES PATENT AND TRADEMARK OFFICE
CERTIFICATE OF CORRECTION

PATENT NO. : 6,169,120 B1
DATED : January 2, 2001
INVENTOR(S) : Beer

It is certified that error appears in the above-identified patent and that said Letters Patent is hereby corrected as shown below:

Claim 15,
Line 53, after "$C_5$-$C_{17}$", insert -- + --.

Signed and Sealed this

Thirteenth Day of November, 2001

Attest:

Nicholas P. Godici

NICHOLAS P. GODICI
Attesting Officer    Acting Director of the United States Patent and Trademark Office